US006583236B1

(12) United States Patent
Giardello et al.

(10) Patent No.: US 6,583,236 B1
(45) Date of Patent: Jun. 24, 2003

(54) POLYOLEFIN COMPOSITIONS HAVING ENHANCED ULTRAVIOLET AND OXIDATIVE RESISTANCE AND METHODS FOR THEIR PRODUCTION AND USE

(75) Inventors: Michael J. Giardello, Pasadena, CA (US); Christopher J. Cruce, Poway, CA (US); Ronald M. Thibault, Osborne, KS (US); George R. Eakin, Osborne, KS (US)

(73) Assignee: Cymetech, LLC, Huntsville, TX (US)

( * ) Notice: Subject to any disclaimer, the term of this patent is extended or adjusted under 35 U.S.C. 154(b) by 0 days.

(21) Appl. No.: 09/498,120

(22) Filed: Feb. 4, 2000

Related U.S. Application Data

(60) Provisional application No. 60/118,847, filed on Feb. 5, 1999.

(51) Int. Cl.[7] .............................. C08F 2/06; C08F 2/08; C08F 4/44

(52) U.S. Cl. ......................... 526/89; 526/161; 526/171; 526/172; 526/283; 502/152; 502/155

(58) Field of Search ................................ 526/171, 172, 526/283, 89, 161; 502/152, 155

(56) References Cited

U.S. PATENT DOCUMENTS

| | | | | |
|---|---|---|---|---|
| 5,312,940 A | | 5/1994 | Grubbs et al. | 556/136 |
| 5,342,909 A | | 8/1994 | Grubbs et al. | 526/171 |
| 5,710,298 A | | 1/1998 | Grubbs et al. | 556/22 |
| 5,728,785 A | | 3/1998 | Grubbs et al. | 526/142 |
| 5,728,917 A | | 3/1998 | Grubbs et al. | 585/653 |
| 5,831,108 A | | 11/1998 | Grubbs et al. | 556/21 |
| 5,880,231 A | | 3/1999 | Grubbs et al. | 526/171 |
| 5,932,664 A | | 8/1999 | Chen et al. | 525/338 |
| 5,969,170 A | | 10/1999 | Grubbs et al. | 556/21 |
| 6,001,909 A | | 12/1999 | Setiabudi | 524/265 |
| 6,020,443 A | * | 2/2000 | Woodson et al. | 526/135 |
| 6,107,420 A | * | 8/2000 | Grubbs et al. | 526/73 |

FOREIGN PATENT DOCUMENTS

| | | | |
|---|---|---|---|
| EP | 0 850 966 | 12/1997 | |
| WO | WO 97/20865 | 6/1997 | C08F/4/80 |
| WO | 97/29135 | 8/1997 | |
| WO | WO 97/29135 | 8/1997 | |
| WO | 97/38036 | 10/1997 | |
| WO | 99/26949 | 6/1999 | |
| WO | WO 99/51344 | 10/1999 | |

OTHER PUBLICATIONS

Nolan et al., “Olefin Metathesis–Active Ruthenium Complexes Bearing a Nucleophilic Carbene Ligand,” J. Am. Chem. Soc., 1999, 121, pp. 2674–2678.

Furstner, et al., “Cationic ruthenium allenylidene complexes as a new class of performing catalysts for ring closing metathesis,” Chem. Commun., 1998, pp. 1315–1316.

* cited by examiner

*Primary Examiner*—Robert D. Harlan
(74) *Attorney, Agent, or Firm*—David Jaffer; Pillsbury Winthrop LLP

(57) ABSTRACT

The invention discloses a method for dispersing a metathesis catalyst in an olefin to produce a catalyst-monomer mixture having a desired catalyst:monomer ratio comprising dispersing the catalyst within a solvent and mixing the dispersed catalyst with an olefin monomer. In preferred embodiments, the catalyst is of the formula $$\begin{array}{c} \quad L \quad\quad R^1 \\ X \diagdown | \quad\quad / \\ \quad M{=}C \\ X^1 \diagup | \quad\quad \diagdown \\ \quad L^1 \quad\quad R \end{array}$$

wherein M is ruthenium or osmium; X and $X^1$ are either the same or different and are any anionic ligand; L and $L^1$ are either the same or different and are neutral electron donor; R and $R^1$ are either the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein each of the substituents is substituted or unsubstituted. Preferably, the olefin monomer is dicyclopentadiene and the solvent is soybean oil or mineral oil.

50 Claims, 9 Drawing Sheets

POLYOLEFIN COMPOSITIONS HAVING ENHANCED ULTRAVIOLET AND OXIDATIVE RESISTANCE AND METHODS FOR THEIR PRODUCTION AND USE

This application claims the benefit of co-pending U.S. Provisional Patent Application Ser. No. 60/118,847, filed Feb. 5, 1999, the contents of which are,herein incorporated by reference.

FIELD OF THE INVENTION

The invention is directed generally to novel polyolefin compositions having enhanced resistance to ultraviolet (UV) exposure and oxidative conditions and to methods for producing and using the same. More specifically, the invention relates to catalyst dispersing carriers and to dicyclopentadiene polymers (poly-DCPD) produced using metathesis catalysts that have been dispersed in a dispersing carrier.

BACKGROUND OF THE INVENTION

It is known to use certain ruthenium and osmium carbene compounds to catalyze olefin metathesis reactions such as, for example, ring opening metathesis polymerization (ROMP), to produce polyolefin compositions. Such olefin metathesis reactions and suitable metathesis catalysts (e.g., ruthenium- or osmium-based catalysts) have been previously described in, for example, U.S. Pat. Nos. 5,312,940, 5,342,909, 5,728,917, 5,710i298, 5,831,108, and 6,001,909; PCT Publications WO 97/20865, WO 97/29135 and WO 99/51344; in United States Provisional Patent Application No. 60/142,713 filed Jul. 7, 1999 entitled "ROMP Reactions Using Imidazolidine-Based Metal Carbene Metathesis Catalysts;" and by Fürstner, Picquet, Bruneau, and Dixneuf in Chemical Communications, 1998, pages 1315–1316, the disclosures of each of which are incorporated herein by reference.

One example of a polyolefin compound that may be produced using the aforementioned metathesis catalysts is poly-DCPD. A problem associated with the polymerization of DCPD is obtaining a homogeneous mixture of metathesis catalyst with DCPD monomer. It has been found that, in order to obtain the desired catalyst:DCPD monomer ratio, it is preferable to pre-mix the catalyst in a small amount of DCPD monomer prior to introduction to and mixing with the remaining amount of DCPD monomer. Such pre-mixing leads to a more homogeneous dispersion of the catalyst in the DCPD monomer and ensures that the catalyst and the monomer are combined in their proper proportions in order to optimize the polymerization reaction. However, it has been determined that poly-DCPD compositions prepared using these catalyst-DCPD mixtures suffer a rapid loss of physical properties, particularly impact properties, with aging. This deterioration is even more pronounced in the presence of ultraviolet (UV) exposure or under oxidative conditions, and is particularly severe in the case of UV weathering with condensation. The deterioration rate can be reduced by the addition of certain traditional antioxidant materials such as, for example, 4,4'-methylenebis(2,6-ditertiary-butylphenol) (Ethanox 702™; Albemarle Corporation), 1,3,5-trimethyl-2,4,6-tris(3,5-di-tert-butyl-4-hydroxybenzyl)benzene (Ethanox 330™; Albemarle Corporation), and octadecyl-3-(3', 5'-di-tert-butyl-4'-hydroxyphenyl)propionate (Irganox $_{1076}$™; Ciba-Geigy). However, these traditional antioxidant materials are typically very expensive.

In light of the foregoing, there exists a need for a means to homogeneously disperse a metathesis catalyst in an olefin (e.g., DCPD) monomer prior to polymerization and for an effective and inexpensive way to enhance the UV and oxidative resistance of the resulting polyolefin (e.g., poly-DCPD) composition.

SUMMARY OF THE INVENTION

The invention relates to novel polyolefin compositions having enhanced UV and oxidative resistance and methods for their production and use. In particular, the invention provides for a dispersing carrier in which a metathesis catalyst may be dispersed prior to mixing with an olefin monomer, in order to optimize the catalyst:olefin monomer ratio as well as to obtain a sufficiently homogeneous catalyst-monomer mixture prior to polymerization.

The dispersing carrier may be any solvent which has a sufficiently high viscosity so as to permit effective dispersion of the catalyst, and which is sufficiently inert and which has a sufficiently high boiling point so that it does not act as a low-boiling impurity in the olefin metathesis reaction. Particularly preferred catalyst dispersing carriers include "oily" or hydrophobic solvents such as, for example, soybean oil or mineral oil. Other preferred catalyst dispersing carriers include high-viscosity hydrophobic hydrocarbons such as, for example, tri-isopropylbenzene (SureSol 450™).

The dispersion of the metathesis catalyst in a catalyst dispersing carrier prior to polymerization permits a sufficiently homogeneous catalyst-monomer mixture. In addition, the catalyst dispersing carrier unexpectedly produces a polyolefin composition having enhanced resistance to UV exposure and oxidative conditions. Specifically, the catalyst dispersing carrier reduces the rate of deterioration of physical properties with aging. The increase in UV and oxidative resistance provided by the dispersing carrier obviates the need for the addition of traditional, expensive antioxidant materials.

One aspect of the invention is a novel polyolefin composition having enhanced UV and oxidative resistance without the need for typical antioxidants. Another aspect is a process for preparing such UV-resistant polyolefin compositions, wherein the process includes the step of dispersing a metathesis catalyst in a catalyst dispersing carrier prior to mixing with the olefin monomer. Yet another aspect is a polyolefin composition prepared using the aforementioned process. A further aspect is an article of manufacture comprising the aforementioned polyolefin composition, such article having enhanced UV and oxidative resistance. These and other aspects of the invention will be apparent to one skilled in the art in light of the figures and the following detailed description of the preferred embodiments.

DETAILED DESCRIPTION OF THE PREFERRED EMBODIMENTS

Figure 1:
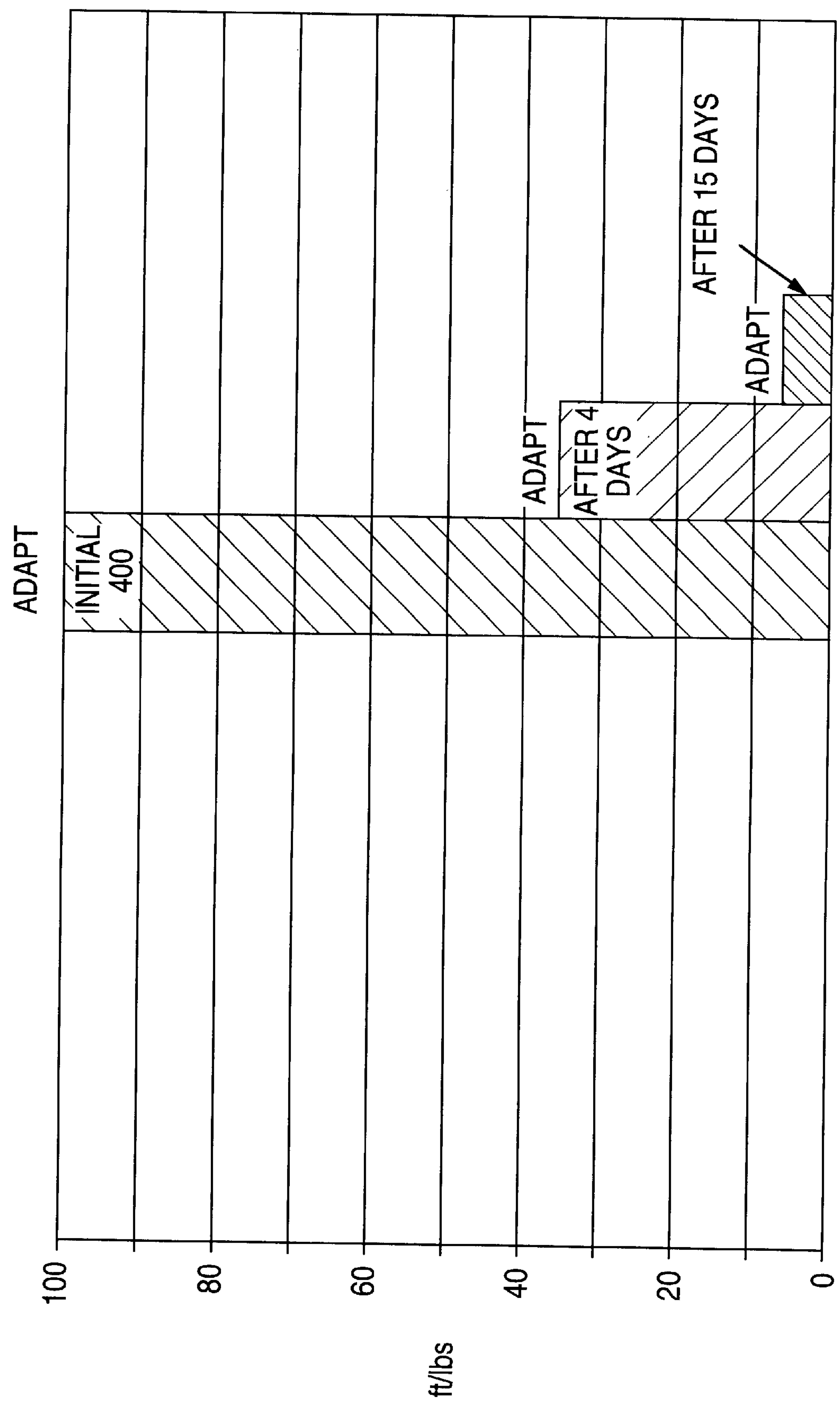
FIG. 1 is a bar graph illustrating the degradation of impact strength (in ft/lbs) of poly-DCPD (ADAPT) with aging in air at room temperature (at 0, 4 and 15 days)

The invention is directed to novel polyolefin compositions having enhanced UV and oxidative resistance, as well as methods for their production and use. More specifically, the invention relates to a catalyst dispersing carrier in which a metathesis catalyst may be mixed or dispersed prior to introduction to and mixing with an olefin monomer. By dispersing the metathesis catalyst within a dispersing carrier, the desired catalyst: olefin monomer ratio may be obtained. In addition, the dispersing carrier ensures that a sufficiently homogeneous catalyst-monomer mixture is obtained prior to initiating the metathesis reaction.

The invention is useful in any of various metathesis reactions including, for example, ROMP reactions. Any of various olefin monomers may be polymerized in the invention. Preferably, the olefin monomer is dicyclopentadiene (DCPD). Various DCPD suppliers and purities may be used such as Lyondell 108 (94.6% purity), Veliscol UHP (99+% purity), B.F. Goodrich Ultreneo® (97% and 99% purities), and Hitachi (99+% purity). Other preferred olefin monomers include other cyclopentadiene oligomers including trimers, tetramers, pentamers, and the like; cyclooctadiene (COD; DuPont); cyclooctene (COE, Alfa Aesar); cyclohexenylnorbornene (Shell); norbornene (Aldrich); norbornene dicarboxylic anhydride (nadic anhydride); norbornadiene (Elf Atochem); and substituted norbornenes including butyl norbornene, hexyl norbomene, octyl norbornene, decyl norbornene, and the like. Preferably, the olefinic moieties include mono-or disubstituted olefins and cycloolefins containing between 3 and 200 carbons. Most preferably, metathesis-active olefinic moieties include cyclic or multicyclic olefins, for example, cyclopropenes, cyclobutenes, cycloheptenes, cyclooctenes, [2.2.1 ]bicycloheptenes, [2.2.2]bicyclooctenes, benzocyclobutenes, cyclopentenes, cyclopentadiene oligomers including trimers, tetramers, pentamers, and the like; cyclohexenes. It is also understood that such compositions include frameworks in which one or more of the carbon atoms carry substituents derived from radical fragments including halogens, pseudohalogens, alkyl, aryl, acyl, carboxyl, alkoxy, alkyl- and arylthiolate, amino, aminoalkyl, and the like, or in which one or more carbon atoms have been replaced by, for example, silicon, oxygen, sulfur, nitrogen, phosphorus, antimony, or boron. For example, the olefin may be substituted with one or more groups such as thiol, thioether, ketone, aldehyde, ester, ether, amine, amide, nitro, carboxylic acid, disulfide, carbonate, isocyanate, phosphate, phosphite, sulfate, sulfite, sulfonyl, carboiimide, carboalkoxy, carbamate, halogen, or pseudohalogen. Similarly, the olefin may be substituted with one or more groups such as $C_1$–$C_{20}$ alkyl, aryl, acyl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, arylthio, $C_1$–$C_{20}$ alkylsulfonyl, and $C_1$–$C_{20}$ alkylsulfinyl, $C_1$–$C_{20}$ alkylphosphate, arylphosphate, wherein the moiety may be substituted or unsubstituted.

These olefin monomers may be used alone or mixed with each other in various combinations to adjust the properties of the olefin monomer composition. For example, mixtures of cyclopentadiene dimer and trimers offer a reduced melting point and yield cured olefin copolymers with increased mechanical strength and stiffness relative to pure poly-DCPD. As another example, incorporation of COD, norbomene, or alkyl norbornene comonomers tend to yield cured olefin copolymers that are relatively soft and rubbery. The polyolefin resins of the invention are amenable to thermosetting and are tolerant of additives, stabilizers, rate modifiers, hardness and/or toughness modifiers, fillers and fibers including, but not limited to, carbon, glass, aramid (e.g., Kevlar® and Twaron®), polyethylene (e.g., Spectra® and Dyneema®), polyparaphenylene benzobisoxazole (e.g., Zylon®), polybenzamidazole (PBI), and hybrids thereof as well as other polymer fibers.

In the preparation of polyolefins, a metathesis catalyst may be pre-mixed with a small amount of olefin monomer prior to mixing with the remaining olefin monomer. This method has been found to lead to better catalyst-monomer mixing. However, even with pre-mixing, the catalyst may not be sufficiently dispersed among the monomer for optimal reaction conditions. Moreover, the resulting poly-DCPD product is somewhat sensitive to WV and oxidative aging. Consequently, the physical properties of the poly-DCPD degrade rather quickly, especially under humid conditions (e.g., UV exposure with water condensation).

The UV and oxidative resistance of poly-DCPD may be improved by the addition of typical antioxidants, such as for example, 4,4'-methylenebis(2,6-di-tertiary-butylphenol) (Ethanox $_{702}$™; Albemarle Corporation), 1,3,5-trimethyl-2,4,6-tris(3,5-di-tert-butyl-4-hydroxybenzyl)benzene (Ethanox 330™; Albemarle Corporation), and octadecyl-3-(3', 5'-di-tert-butyl-4'-hydroxyphenyl)propionate (Irganox $_{1076}$™; Ciba-Geigy). However, these antioxidants are usually expensive and are, therefore, impractical for certain commercial applications.

Exemplary catalysts have been previously described in, for example, U.S. Pat. Nos. 5,312,940, 5,342,909, 5,728,917, 5,710,298, 5,831,108, and 6,001,909; PCT Publications WO 97/20865, WO 97/29135 and WO 99/51344; in United States Provisional Patent Application No. 60/142,713 filed Jul. 7, 1999 entitled "ROMP Reactions Using Imidazolidine-Based Metal Carbene Metathesis Catalysts;" and by Fürstner, Picquet, Bruneau, and Dixneuf in Chemical Communications, 1998, pages 1315–1316, the disclosures of each of which are incorporated herein by reference.

Any suitable metathesis catalyst may be used. Briefly, the ruthenium and osmium carbene catalysts possess metal centers that are formally in the +2 oxidation state, have an electron count of 16, are penta-coordinated, and are of the general formula

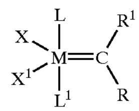

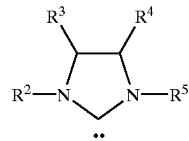

wherein:

M is ruthenium or osmium;

X and $X^1$ are each independently any anionic ligand;

L and $L^1$ are each independently any neutral electron donor ligand;

R and $R^1$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of these catalysts, the R substituent is hydrogen and the $R^1$ substituent is selected from the group consisting $C_1$–$C_{20}$ alkyl, $C_2$–$C_{20}$ alkenyl, and aryl. In even more preferred embodiments, the $R^1$ substituent is phenyl or vinyl, optionally substituted with one or more moieties selected from the group consisting of $C_1$–$C_5$ alkyl, $C_1$–$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl.

In preferred embodiments of these catalysts, L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L and $L^1$ are each a phosphine of the formula $PR^3R^4R^5$, where $R^3$, $R^4$, and $R^5$ are each independently aryl or $C_1$–$C_{10}$ alkyl, particularly primary alkyl, secondary alkyl or cycloalkyl . In the most preferred embodiments, L and $L^1$ ligands are each selected from the group consisting of —P(cyclohexyl)$_3$, —P(cyclopentyl)$_3$, —P(isopropyl)$_3$, and —P(phenyl)$_3$. Another preferred embodiment of the catalyst is where L is any neutral electron donor and $L^1$ is an imidazolidine ligand. In certain embodiments, $L^1$ may have the general formula wherein: $R^2$, $R^3$, $R^4$, and $R^5$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_,$-$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. $R^3$ and $R^4$ may also together form a cycloalkyl or an aryl moiety. A preferred embodiment is where $R^3$ and $R^4$ are both hydrogen or phenyl and $R^2$ and $R^5$ are each independently substituted or unsubstituted aryl. In addition, L and $L^1$ may together comprise a bidentate ligand.

In preferred embodiments of these catalysts, X and $X^1$ are each independently hydrogen, halide, or one of the following groups: $C_1$–$C_{20}$ alkyl, aryl, $C_1$–$C_{20}$ alkoxide, aryloxide, $C_3$-$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride. In addition, X and $X^1$ may together comprise a bidentate ligand.

The catalyst:olefin monomer ratio in the invention is preferably is in a range of about 1:100 to about 1: 1,000,000. More preferably, the catalyst:monomer ratio is in a range of about 1:1,000 to about 1: 150,000 and, most preferably, is in a range of about 1:3,000 to about 1:60,000. Particularly preferred metal catalysts include, but are not limited to, bis(tricyclohexylphosphine) benzylidene ruthenium dichloride, bis(tricyclohexylphosphine) dimethylvinylmethylidene ruthenium dichloride, bis(tricyclopentylphosphine) dimethylvinylmethylidene ruthenium dichloride, (tricyclohexylphosphine)(1,3-dimesityl-4,5-dihydroimidazol-2-ylidene) benzylidene ruthenium dichloride, (tricyclopentylphosphine)(1,3-dimesityl-4,5-dihydroimidazol-2-ylidene) dimethylvinylmethylidene ruthenium dichloride, (tricyclohexylphosphine) (1,3-dimesityl-4,5-dihydroimidazol-2-ylidene) dimethylvinylmethylidene ruthenium dichloride, (tricyclohexylphosphine) (1,3-dimesitylimidazol-2-ylidene) benzylidene ruthenium dichloride, (tricyclopentylphosphine)(1,3-dimesitylimidazol-2-ylidene) dimethylvinylmethylidene ruthenium dichloride, and (tricyclohexylphosphine) (1,3-dimesitylimidazol-2-ylidene) dimethylvinylmethylidene ruthenium dichloride. A suitable inhibitor such as, for example, triphenylphosphine (TPP), tricyclopentylphosphine,-tricyclohexylphosphine, triisopropylphosphine, pyridine, or other Lewis base, may be added.

It is preferred that the metathesis catalyst is homogeneously dispersed in the olefin monomer for optimal reaction conditions. However, because of the very low catalyst:monomer ratios typically involved, it is often difficult to obtain sufficient dispersion of the metathesis catalyst in the olefin monomer. Dispersion of the metathesis catalyst may be improved by pre-mixing the catalyst with a small amount of the olefin monomer prior to mixing with the remaining olefin monomer. However, using this pre-mixing method, the catalyst dispersion is sometimes insufficiently homogeneous for optimal reaction conditions.

Dispersion of the metathesis catalyst in a catalyst dispersing carrier prior to initiation of the polymerization reaction provides a sufficiently homogeneous catalyst-monomer mixture. In most cases, the dispersion will be adequately homogenous if its appearance is visually homogenous to the human eye with no observable mottling, settling, or separation of a distinct liquid layer. The dispersing carrier of the invention is a solvent having a sufficiently high viscosity so as to provide effective dispersion of the metathesis catalyst. Those skilled in the art are capable of determining the proper carrier viscosity based upon particle size, morphology, and density of the particular catalyst being used and the amount of time that the catalyst/carrier dispersion must remain homogenous to meet the requirements of the particular processing technique utilized. Generally, the viscosity range is in the range of about 0.1 to about 200 centistokes. Preferably the viscosity range is in the range of about 0.5 to about 50 centistokes and most preferably is in the range of about 2 to about 10 centistokes. Preferably, the dispersing carrier is also inert and has a boiling point high enough so that it does not act as a low-boiling impurity that causes foaming or bubbling in the exothermic olefin metathesis reaction. In general, the boiling point of the carrier should be at least as high as the boiling point of the olefin monomer to which it will be added and preferably should also be somewhat higher than the highest temperature that the mixture will experience during the processing technique utilized. One skilled in the art can measure the temperature and pressure conditions existing within a particular item of processing equipment or within a mold and thereby determine the minimum boiling point required for the carrier.

Particularly preferred catalyst dispersing carriers include "oily" or hydrophobic solvents such as, for example, soybean oil or mineral oil. Other preferred catalyst dispersing carriers include high-viscosity hydrophobic hydrocarbons such as, for example, tri-isopropylbenzene (SureSol $_{450}$™).

The dispersing carrier may be present in an amount of about 0. 1% to about 15% by weight of the olefin monomer. Preferably, the dispersing carrier is present in an amount of about 1% to about 5% by weight of the olefin monomer and, most preferably, in an amount of about 1% to about 3% by weight of the olefin monomer. The metathesis catalyst is dispersed in the dispersing carrier with stirring or mixing. The resulting catalyst-carrier dispersion is mixed with olefin monomer to obtain the desired catalyst:monomer ratio.

In addition to the advantages associated with catalyst dispersion, the addition of a dispersing carrier unexpectedly imparts the resulting polyolefin composition with enhanced UV and oxidative resistance. More specifically, the dispersing carrier reduces the rate of degradation of physical properties (e.g., tensile, flexural, and notched Izod impact properties) with aging, either at room or elevated temperatures. The increase in UV and oxidative resistance provided by the dispersing carrier obviates the need for the addition of expensive antioxidants. Accordingly, the invention provides for parts or articles of manufacture having enhanced UV-resistant properties. Such articles may be manufactured using standard molding techniques, such as resin transfer molding (RTM). Various molding techniques are described, for example, in PCT Publication WO 97/20865, the disclosure of which is incorporated herein by reference. In addition, pigments or dyes may optionally be added to the polyolefin composition for applications where color is desired.

For the purposes of clarity, the specific details of the invention will be illustrated with reference to especially preferred embodiments. However, it should be appreciated that these embodiments and examples are for the purposes of illustration only and are not intended to limit the scope of the invention.

EXAMPLES

Comparative Example

DCPD monomer (Velsicol Chemical Company; 99% purity) was used to make a polymerization mixture by adding 0.06 g triphenylphosphine (TPP)/64 g DCPD and 1 g $C1_2(PCy_3)_2Ru{=}C(Ph)(H)$ (C823 catalyst)/7500 g DCPD. No antioxidant or catalyst dispersing carrier was included in this formulation. The C823 catalyst was first pre-mixed with stirring in about 10 g DCPD into which the TPP had been previously dissolved. This pre-mixed catalyst solution was then added to the remaining DCPD monomer. This mixture was immediately poured at room temperature (RT) without air entrapment into a pre-warmed (100–120° F.) standard plaque mold. Polymer plaques were post-cured at 250° F. for 1 hour.

Samples of the polymer plaques were then prepared. Samples were immediately tested at room temperature (72° F.) for impact properties. Tests of impact strength were repeated at 4 days and 15 days after polymerization. Samples were stored at RT in open air.

The degradation of impact strength of the poly-DCPD is shown graphically in FIG. 1. Falling dart impact tests indicate a very high initial impact strength value for the poly-DCPD sample (ADAPT), which deteriorates rapidly to about 35% of its initial value after 4 days and to about 7% of its initial value after 15 days in air at RT.

EXAMPLE 1

Poly-DCPD samples were prepared using the same procedure described in the Comparative Example above, except that an antioxidant (Ethanox 702) was added and mineral and soybean oil were used as dispersing carriers for the C823 catalyst, instead of pre-mixing the C823 catalyst into a small amount of DCPD monomer:

DCPD monomer (Velsicol Chemical Company; 99% purity) was used to make polymerization mixtures by adding 0.06 g TPP/64 g DCPD, 1 g C823/7500 g DCPD, and 4 g Ethanox 702/96 g DCPD. The C823 catalyst was first dispersed in the dispersing carrier (either soybean or mineral oil) with stirring at 1, 2 and 3 weight percent (wt%) carrier (based on.DCPD monomer). The catalyst-carrier dispersion was added with mixing into the DCPD monomer into which the TPP inhibitor and Ethanox 702 antioxidant had been previously dissolved. The C823 catalyst-carrier mixture was added to the DCPD monomer either immediately or after a 72 hour or 7 day delay. A control (Neat) was prepared by adding the C823 catalyst directly to the DCPD monomer mixture (with no dispersing carrier) with rapid stirring. The catalyzed mixtures were immediately poured at room temperature without air entrapment into a pre-warmed (100–120° F.) standard plaque mold. All polymer plaques were post-cured at 250° F. for 1 hour.

The tensile and flexural properties of the poly-DCPD samples were immediately measured at room temperature with various levels of carrier. The test results are reported in Table 1 (Flexural Properties) and Table 2 (Tensile Properties) below. The flexural strength, flexural modulus, and tensile strength, in particular, did not change significantly with the addition of mineral oil up to 3 wt% or with the substitution of soybean oil for mineral oil at 1 and 2 wt%. In addition, the physical property values of the poly-DCPD samples made with C823 catalyst dispersed in 1% mineral oil were essentially unchanged even where the C823 catalyst-carrier dispersion was allowed to age for 72 hours or 7 days prior to mixing with the DCPD monomer.

DCPD; and 4 g Ethanox 702/96 g DCPD. The C823 was first dispersed in a dispersing carrier with stirring at 1, 2 and 3 wt% carrier (based on DCPD monomer). The C823 catalyst-carrier mixture was then added immediately with mixing into the DCPD monomer into which the TPP inhibitor and Ethanox 702 antioxidant had been previously dissolved. Velsicol 99% DCPD controls without carrier (Neat) were made by simply adding the C823 directly into the DCPD monomer mixture with rapid stirring. The catalyzed mixtures were immediately poured at room temperature without air entrapment into a pre-warmed (100–120° F.) standard plaque mold. All polymer plaques were post-cured at 250° F. for 1 hour. Test samples of the polymer plaques were then prepared and immediately measured at room temperature (720 F) for tensile and flexural properties.

TABLE 1

FLEXURAL PROPERTIES

| POLY-DCPD SAMPLE | FLEXURAL STRENGTH (psi) | FLEXURAL MODULUS (psi) | FLEXURAL YIELD STRENGTH (psi) | FLEXURAL OFF-YIELD STRENGTH (psi) | SAMPLE WIDTH (in.) | SAMPLE THICKNESS (in.) |
|---|---|---|---|---|---|---|
| Neat | 14278 ± 269.9 | 33620 ± 7815.5 | 598.2 ± 9.7 | 227.9 ± 9.4 | 0.503 ± 0.002 | 0.276 ± 0.002 |
| 1% Mineral Oil | 15210 ± 255.0 | 348400 ± 7079.4 | 630.0 ± 12.8 | 271.7 ± 14.8 | 0.501 ± 0.001 | 0.269 ± 0.002 |
| 2% Mineral Oil | 15188 ± 251.4 | 348329 ± 7811.2 | 628.5 ± 13.2 | 243.7 ± 20.5 | 0.503 ± 0.001 | 0.275 ± 0.002 |
| 3% Mineral Oil | 1588.4 ± 167.3 | 358904 ± 2885.8 | 653.6 ± 13.1 | 317.8 ± 20.6 | 0.501 ± 0.002 | 0.264 ± 0.003 |
| 1% Soybean Oil | 15272 ± 245.5 | 347472 ± 5019.9 | 633.5 ± 10.7 | 255.1 ± 17.7 | 0.501 ± 0.002 | 0.265 ± 0.003 |
| 2% Soybean Oil | 15022 ± 172.4 | 347454 ± 3723.9 | 626.9 ± 8.4 | 243.0 ± 26.2 | 0.502 ± 0.001 | 0.274 ± 0.002 |
| 1% Mineral Oil (72 hr. delay) | 14999 ± 155.9 | 343555 ± 3701.3 | 623.5 ± 6.2 | 290.3 ± 12.9 | 0.502 ± 0.001 | 0.274 ± 0.002 |
| 1% Mineral Oil (7 day delay) | 15332 ± 411.1 | 347904 ± 12945.7 | 641.7 ± 19.0 | 256.2 ± 34.0 | 0.499 ± 0.006 | 0.265 ± 0.002 |

TABLE 2

TENSILE PROPERTIES

| POLY-DCPD SAMPLE | TENSILE STRENGTH (psi) | PERCENT ELONGATION (%) | TENSILE MODULUS (psi) | SAMPLE WIDTH (in.) | SAMPLE THICKNESS (in.) |
|---|---|---|---|---|---|
| Neat | 9933 ± 22.2 | 12.7 ± 0.2 | 66983.9 ± 6095.2 | 0.498 ± 0.003 | 0.265 ± 0.008 |
| 1% Mineral Oil | 10346 ± 52.3 | 12.8 ± 0.3 | 85750.9 ± 22154.7 | 0.496 ± 0.001 | 0.265 ± 0.003 |
| 2% Mineral Oil | 10553 ± 94.3 | 13 ± 0.2 | 64099.2 ± 7707.8 | 0.496 ± 0.003 | 0.273 ± 0.005 |
| 3% Mineral Oil | 10752 ± 46.0 | 13 ± 0.2 | 76629.9 ± 24871.4 | 0.498 ± 0.002 | 0.271 ± 0.004 |
| 1% Soybean Oil | 10354 ± 34.9 | 13 ± 0.2 | 95494.6 ± 22651.3 | 0.498 ± 0.002 | 0.272 ± 0.004 |
| 2% Soybean Oil | 10519 ± 15.6 | 13 ± 0.1 | 60784.6 ± 3963.9 | 0.496 ± 0.001 | 0.266 ± 0.006 |
| 1% Mineral Oil (72 hr. delay) | 10473 ± 68.7 | 13 ± 0.0 | 84406.2 ± 28290.6 | 0.462 ± 0.048 | 0.265 ± 0.008 |
| 1% Mineral Oil (7 day delay) | 10419 ± 65.8 | 12.6 ± 0.3 | 107443.2 ± 20982.3 | 0.495 ± 0.001 | 0.265 ± 0.002 |

The values in Tables 1 and 2 are average values for five (5) samples. The "±" values represent standard deviations.

EXAMPLE 2

Poly-DCPD samples were prepared essentially according to the procedure described in the Example I above. A dispersing carrier (mineral oil, diethylbenzene (SureSol 151), or tri-isopropylbenzene (SureSol 450)) was used to disperse the C823 catalyst, instead of mixing the C823 catalyst with a small amount of DCPD monomer.

Figure 2:
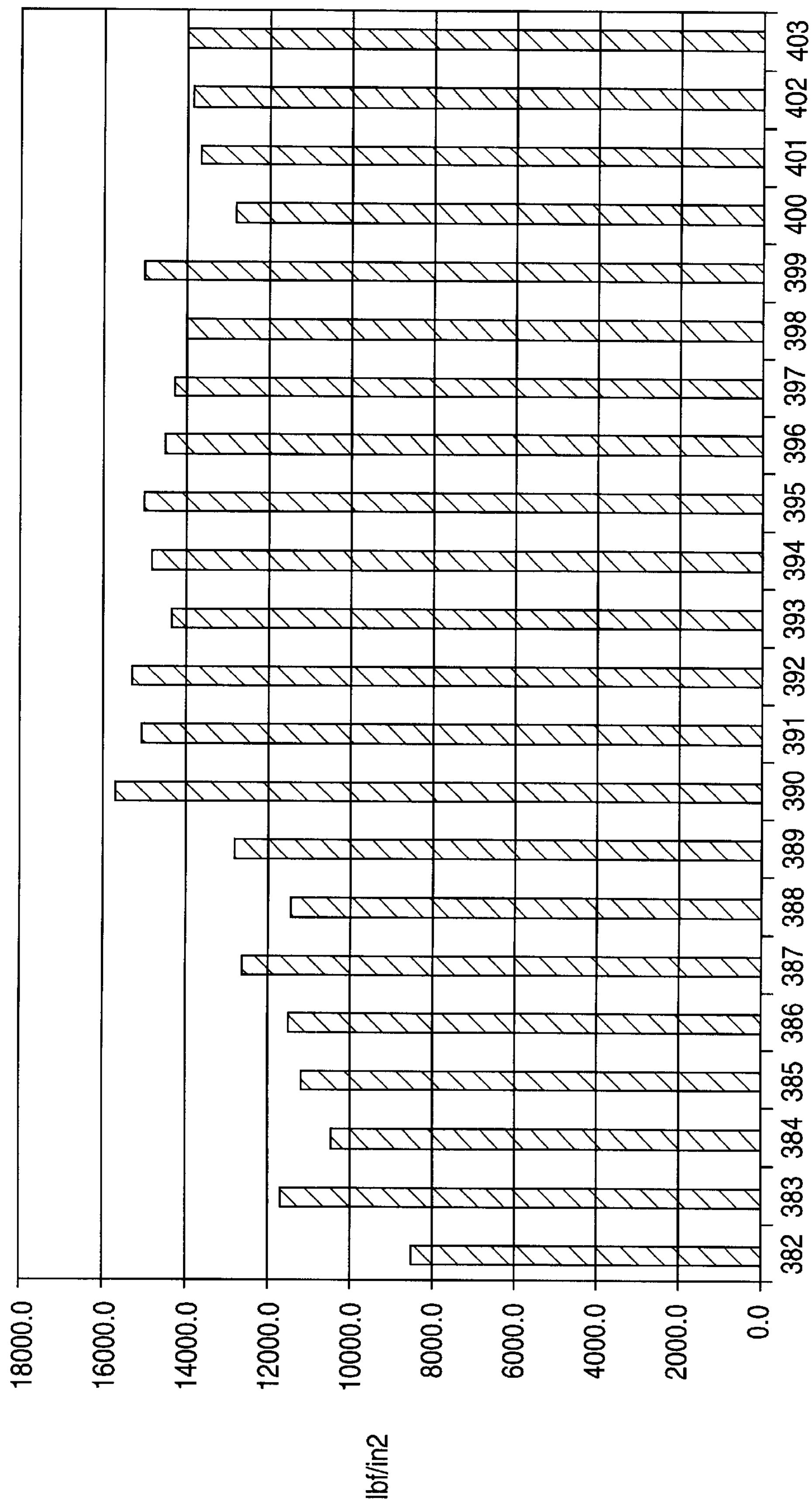
FIG. 2 is a bar graph illustrating the flexural strength (in lbf/in$^2$) for various poly-DCPD samples described in Example 2.
Figure 3:
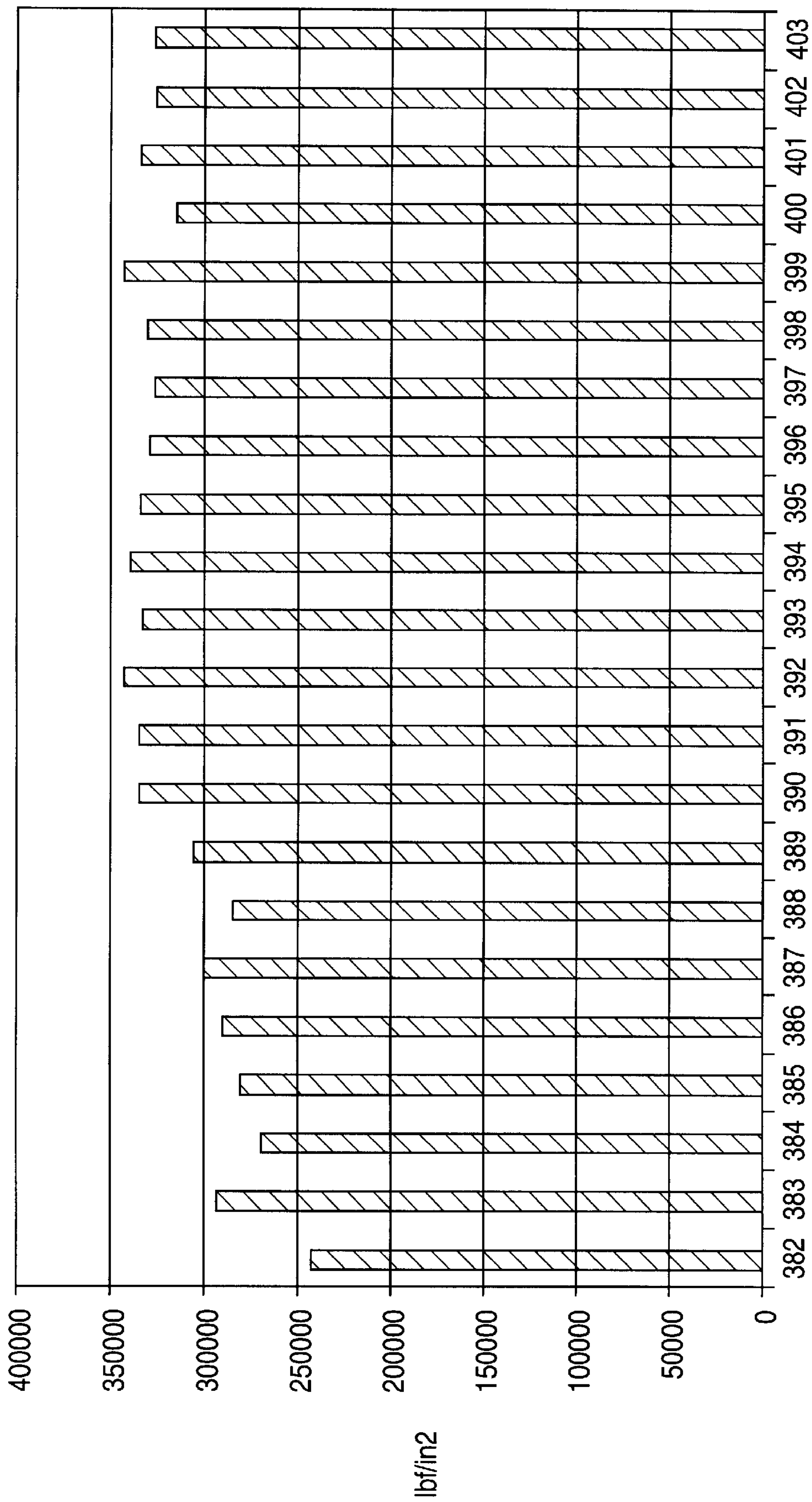
FIG. 3 is a bar graph illustrating the elastic modulus (in lbf/in$^2$) for various poly-DCPD samples described in Example 2.
Figure 4:
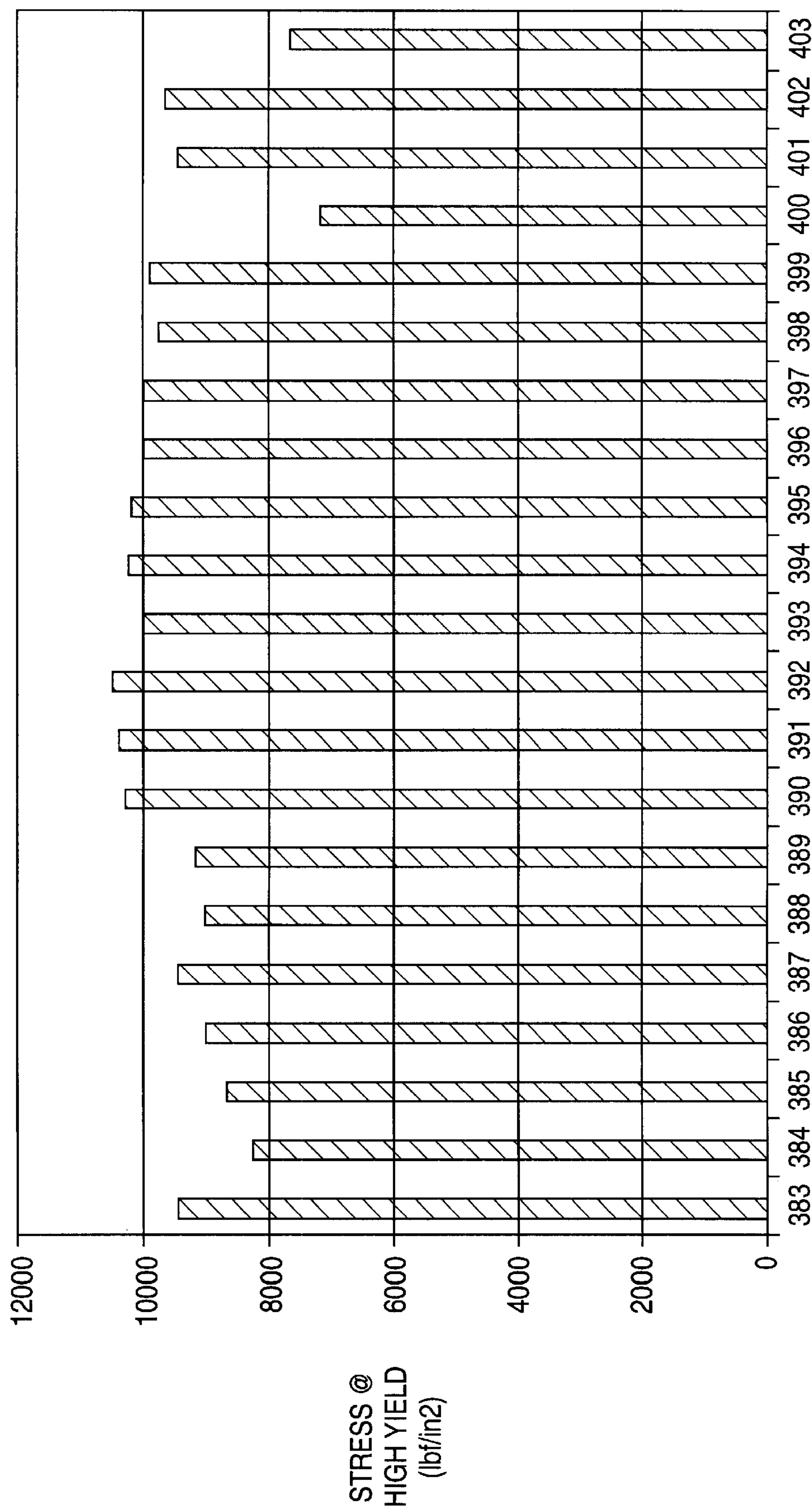
FIG. 4 is a bar graph illustrating the high-yield tensile strength (in lbf/in$^2$) for various poly-DCPD samples described in Example 2.

Two suppliers of DCPD monomer were tested: (1) Velsicol Chemical Company (99% purity); and (2) B. F. Goodrich (two grades: 99% and 97% purity). Each of these three DCPD monomers were used to make polymerization mixtures by adding 0.06 g TPP/64 g DCPD; 1 g C823/7500 g The tensile and flexural strength and the modulus of elasticity were measured for each sample, as reported in FIGS. 2–4. The sample number references used in FIGS. 2–4 are as follows:

382 Velsicol 99% DCPD with 1% SureSol 151
383 Velsicol 99% DCPD with 1% Mineral Oil
384 Velsicol 99% DCPD with 2% Mineral Oil
385 Velsicol 99% DCPD with 3% Mineral Oil
386 Velsicol 99% DCPD with 1% SureSol 450
387 Velsicol 99% DCPD with 2% SureSol 450
388 Velsicol 99% DCPD with 3% SureSol 450
389 Velsicol Neat
390 B. F. Goodrich 99% DCPD with 1% Mineral Oil
391 B. F. Goodrich 99% DCPD with 2% Mineral Oil 392 B. F. Goodrich 99% DCPD with 3% Mineral Oil 393 B. F. Goodrich 99% DCPD with 1% SureSol 450

394 B. F. Goodrich 99% DCPD with 2% SureSol 450

395 B. F. Goodrich 99% DCPD with 3% SureSol 450

396 B. F. Goodrich 99% DCPD Neat

397 B. F. Goodrich 97% DCPD Neat

398 B. F. Goodrich 97% DCPD with 1% Mineral Oil

399 B. F. Goodrich 97% DCPD with 2% Mineral Oil

400 B. F. Goodrich 97% DCPD with 3% Mineral Oil

401 B. F. Goodrich 97% DCPD with 1% SureSol 450

402 B. F. Goodrich 97% DCPD with 2% SureSol 450

403 B. F. Goodrich 97% DCPD with 3% SureSol 450

All values for poly-DCPD samples prepared with either mineral oil or SureSol 450 as a dispersing carrier were essentially equivalent and, in most cases, improved over the control (Neat) polymer prepared with C823 alone (with no dispersing carrier). Values for poly-DCPD samples prepared using B.F. Goodrich 97% DCPD were slightly reduced compared to the control (Neat), except for tensile strength at 3 wt% of carrier, but were still acceptable. No significant difference was observed between SureSol 450 and mineral oil carriers, except that SureSol 450 was not as effective in maintaining a dispersion due to its lower viscosity. SureSol 151 appeared to react exothermically with the C823 catalyst as the C823 was dispersed in it. Only one plaque was made with SureSol 151, because demold time was considerably longer than expected and the physical properties of the poly-DCPD samples were inferior to those with the other dispersing carriers.

EXAMPLE 3

Poly-DCPD samples were prepared using B.F. Goodrich 99% DCPD monomer according to the procedure described in Example 1 above, using mineral oil or SureSol 450 as a dispersing carrier for the C823 catalyst and, in some cases, omitting the Ethanox 702 antioxidant (as indicated below).

Samples were measured at room temperature (72° F.) for tensile, flexural, and notched Izod impact properties. The results are reported in FIGS. 5–9. The sample number references used in FIGS. 5–9 are as follows:

413 B.F. Goodrich 99% DCPD with 1% Mineral Oil and No Antioxidant

414 B.F. Goodrich 99% DCPD with 1% Mineral Oil and Antioxidant

415 B.F. Goodrich 99% DCPD with 1% SureSol 450 and No Antioxidant

416 B.F. Goodrich 99% DCPD with 1% SureSol 450 and Antioxidant

The flexural strength, tensile strength, modulus of elasticity, and notched Izod values were measured after the following sample conditioning (indicated in the sample number references used in FIGS. 5–9):

A Room Temperature

D UV exposure in Weatherometer (with water condensation) for about 670 hours, rotating weekly E UV exposure in Weatherometer (with water condensation) for about 1340 hours, rotating weekly M 1 hour in oven at 350° F.

Figure 5:
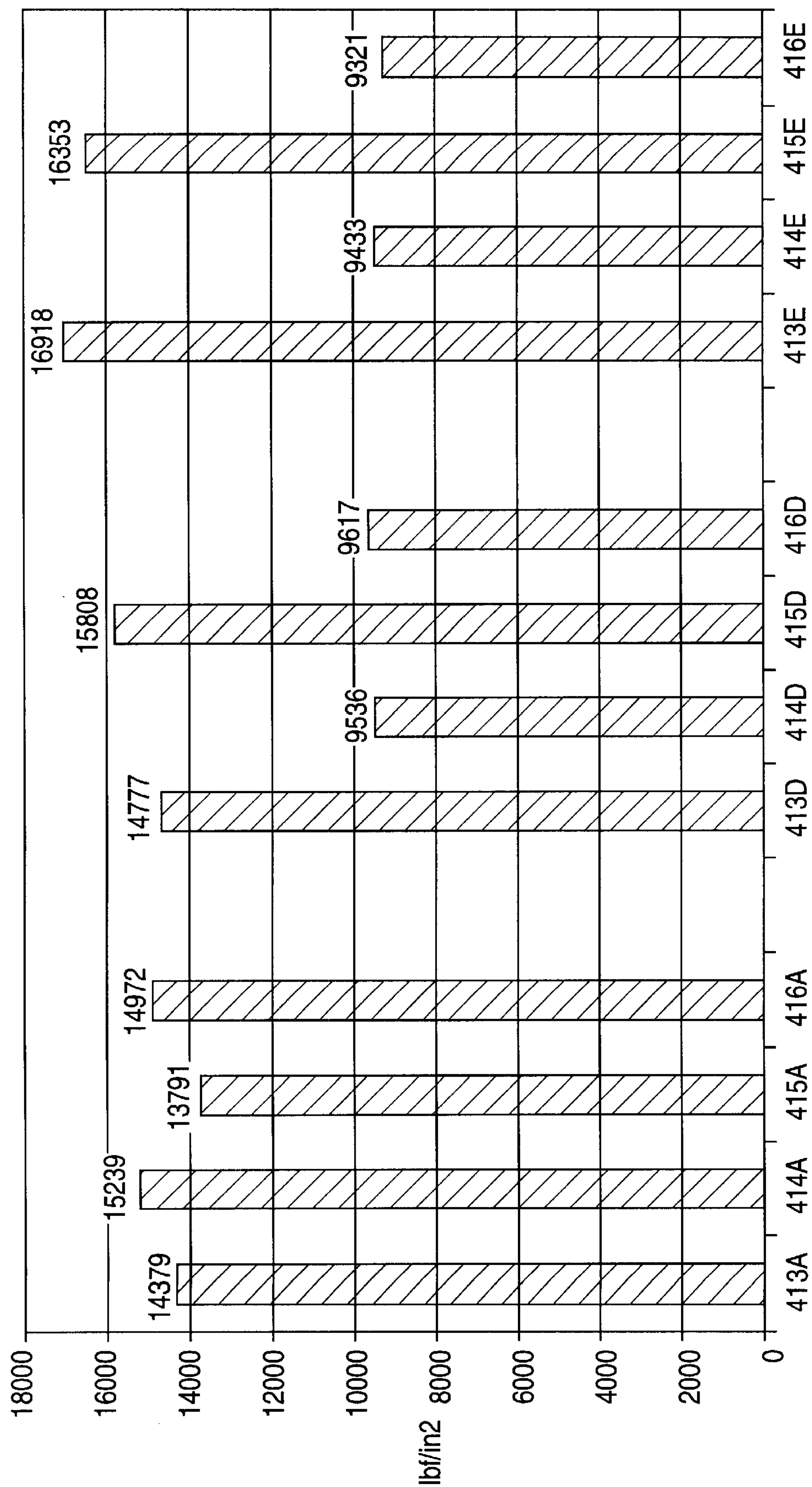
FIG. 5 is a bar graph illustrating the 3-point bend flexural strength (in lbf/in$^2$) for various poly-DCPD samples, with and without UV exposure, as described in Example 3.
Figure 6:
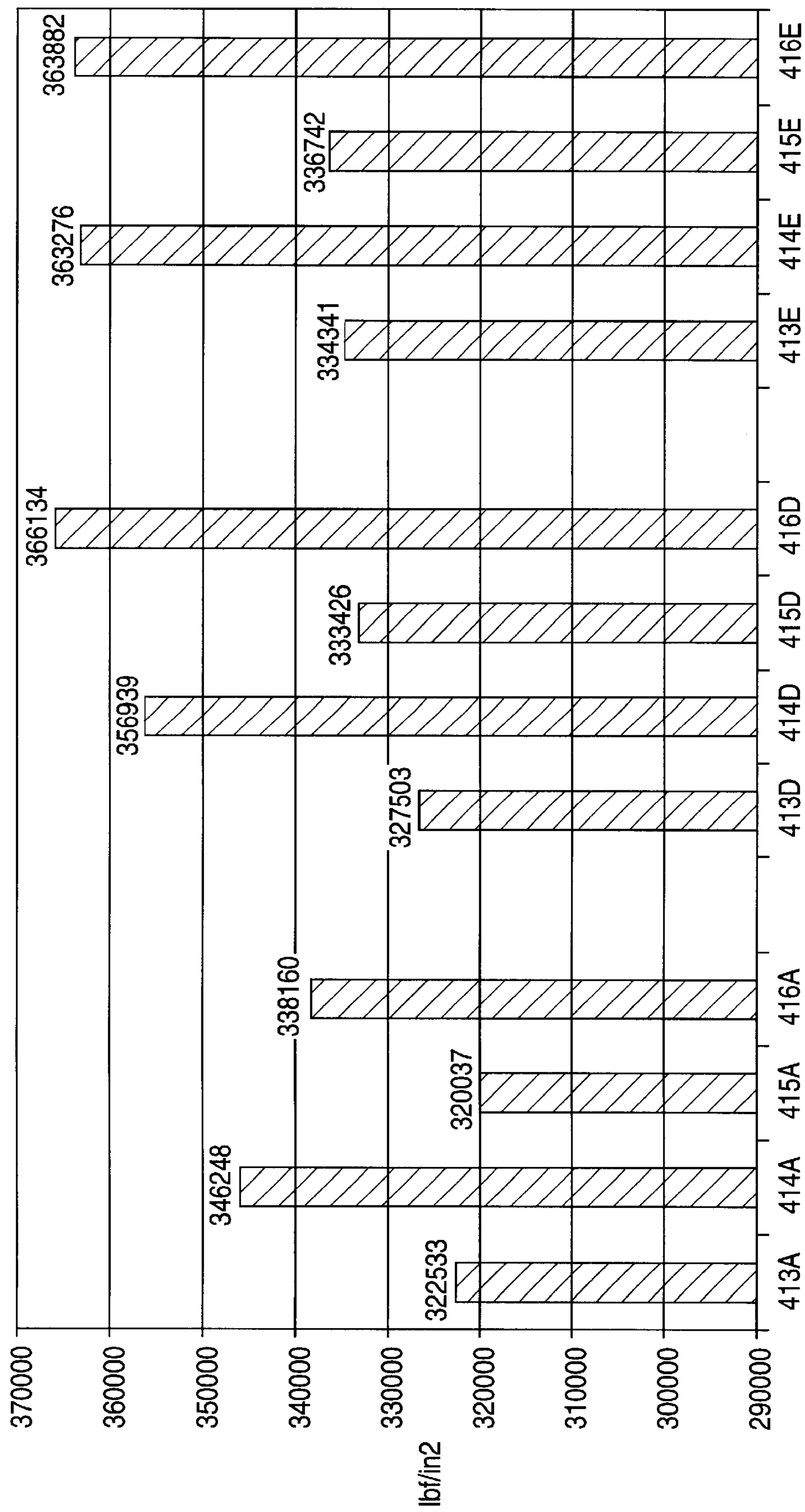
FIG. 6 is a bar graph illustrating the elastic modulus (in lbf/in$^2$) for various poly-DCPD samples, with and without UV exposure, as described in Example 3.

The flexural and tensile strength of all four poly-DCPD samples (sample nos. 413–416; see FIGS. 5 and 7, respectively) were nearly identical at 0 hours exposure, but the modulus of elasticity was higher for the polymer samples with antioxidant (sample nos. 414 and 416; see FIG. 6).

Figure 7:
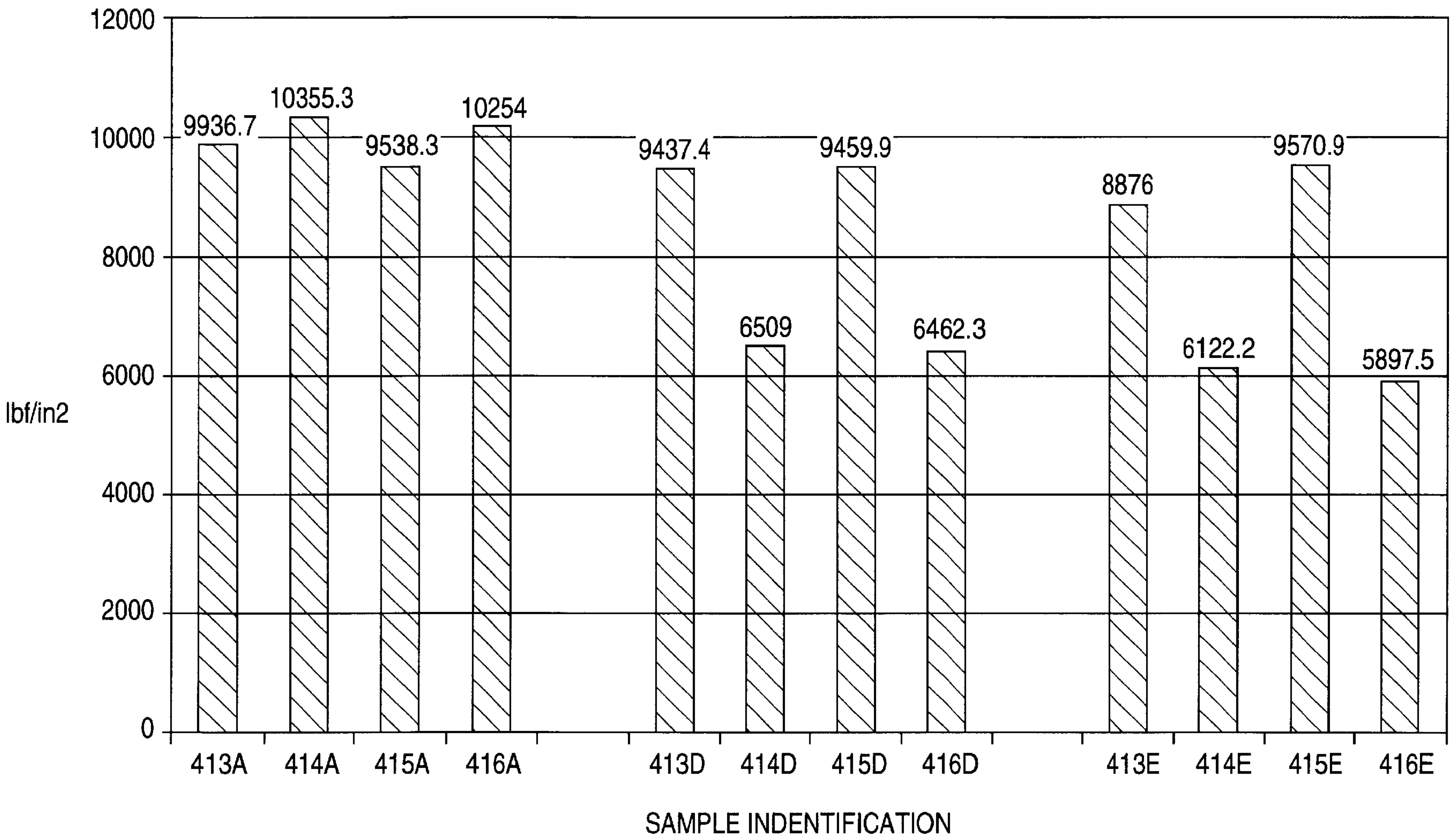
FIG. 7 is a bar graph illustrating the tensile strength (in lbf/in$^2$) for various poly-DCPD samples, with and without UV exposure, as described in Example 3.

Exposure to UV (sample conditions D and E) created a significant decrease in the flexural and tensile strengths for the polymers with antioxidant (sample nos. 414 and 416), but not for the polymers without antioxidant (sample nos. 413 and 415) (see FIGS. 5 and 7).

Figure 8:
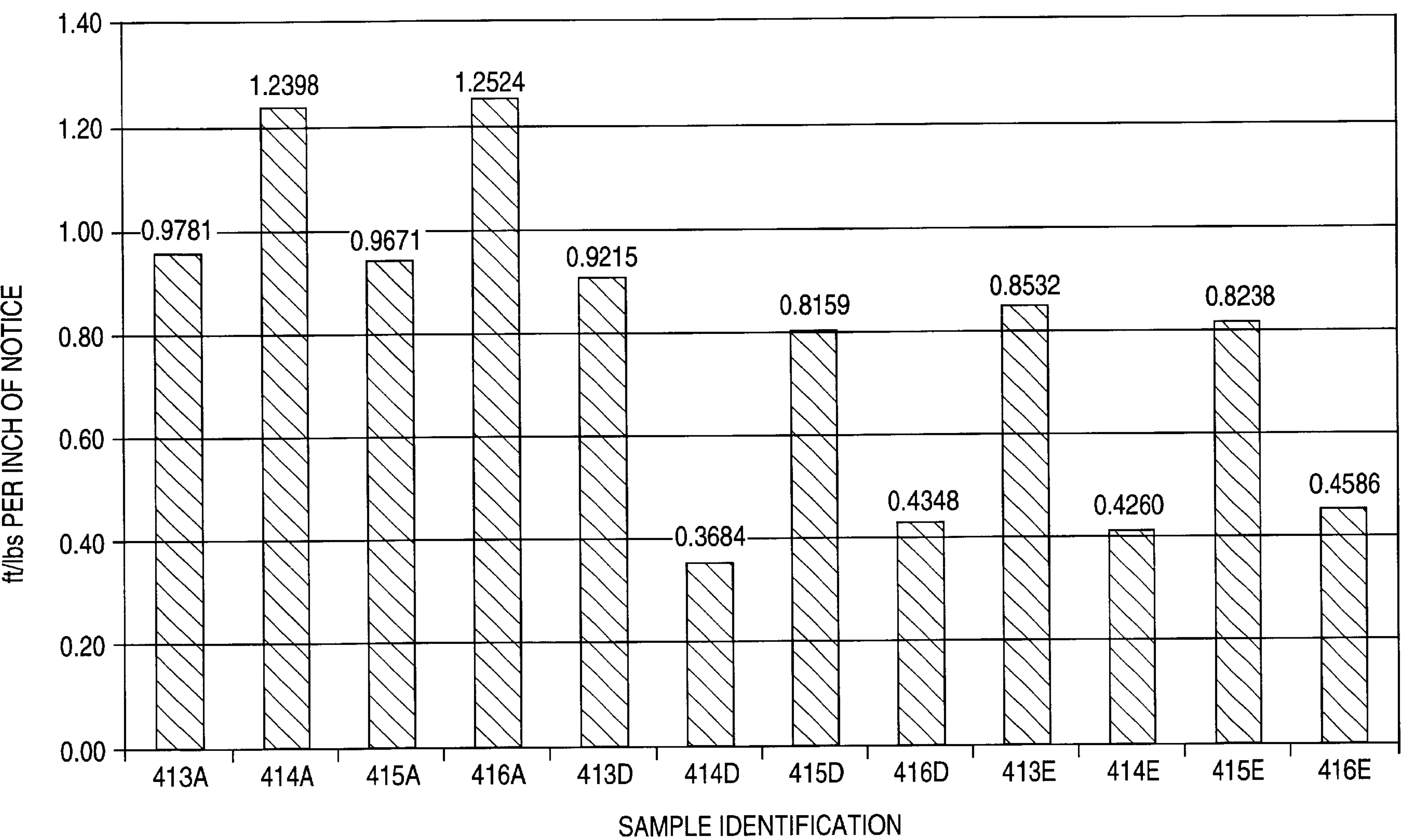
FIG. 8 is a bar graph illustrating the notched Izod values (in ft/lbs per inch of notch) for various poly-DCPD samples, with and without UV exposure, as described in Example 3.
Figure 9:
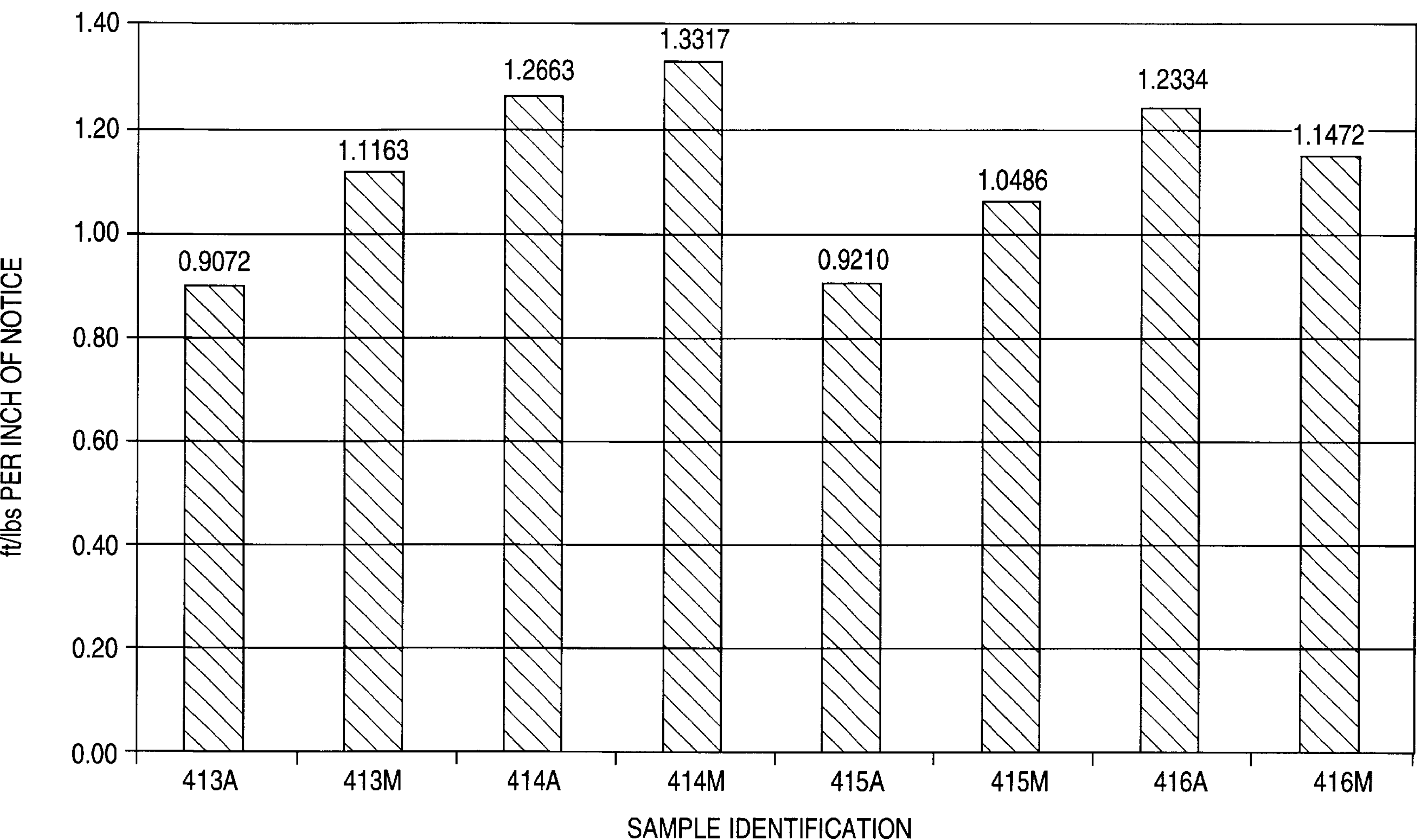
FIG. 9 is a bar graph illustrating the notched Izod values (in ft/lbs per inch of notch) for various poly-DCPD samples, with and without heating for one hour at 350° C., as described in Example 3.

A comparison of notched Izod impact values for RT conditioning (sample condition A) for each polymer showed that those polymers with antioxidant (sample nos. 414 and 416) had somewhat higher impact values than those without antioxidant (sample nos. 413 and 415) (see FIG. 8). The notched Izod impact values for polymers with antioxidant, measured after UV exposure (sample conditions D and E), dropped to about half of the values found for the polymers without antioxidant, values approximately one-third their pre-exposure values. On the other hand, the notched Izod impact values for the polymers without antioxidant (sample nos. 413 and 415) decreased by only about 10% from their pre-exposure values (see FIG. 8).

A comparison of notched Izod impact values (see FIG. 9) for RT conditioning (sample condition A) and for 350° F. post-curing (sample condition M) suggests that the post-cure step improved the impact resistance for three of the four samples (i.e., sample nos. 413–415).

EXAMPLE 4

Poly-DCPD samples were prepared using B.F. Goodrich 99% DCPD monomer according to the procedure described in Example 3 above, except that bis(tricyclopentyl-phosphine) dimethylvinylmethylidene ruthenium dichloride was used instead of the C823 catalyst. The samples are identified as follows:

I DCPD with 1% Mineral Oil and No Antioxidant

II DCPD with 1% Mineral Oil and Antioxidant

III DCPD with 1% SureSol 450 and No Antioxidant

IV DCPD with 1% SureSol 450 and Antioxidant

The flexural strength, modulus of elasticity, and notched Izod values were measured after the following sample conditioning:

A Room Temperature

B UV exposure in Weatherometer (with water condensation) for about 677 hours, rotating weekly The values measured are summarized in the following table:

| Sample | Flexural Strength (psi) | Modulus of Elasticity (psi) | Notched Izod (ft · lb/in) |
|---|---|---|---|
| I - A | 13,171 | 280,002 | 1.3020 |
| I - B | 12,638 | 272,238 | 0.6640 |
| II - A | 11,587 | 273,255 | 1.6470 |
| II - B | 13,774 | 283,899 | 0.4990 |
| III - A | 14,049 | 277,682 | 1.4050 |
| III - B | 14,385 | 268,954 | 0.5280 |
| IV - A | 14,541 | 297,833 | 1.1900 |
| IV - B | 10,962 | 305,651 | 0.3939 |

As in Example 3, the impact performance of the samples without added antioxidant was found be more resistant to aging than for those samples with added antioxidant, especially for the samples prepared using the mineral oil carrier.

What is claimed is:

1. A method for dispersing a metathesis catalyst in an olefin to produce a sufficiently homogenous catalyst-monomer mixture having a desired catalyst:monomer ratio comprising:

dispersing the catalyst within a solvent, wherein the solvent has a sufficiently high viscosity to effect a sufficiently homogenous dispersion of the catalyst; and mixing the dispersed catalyst with an olefin monomer.

2. The method of claim 1 wherein the olefin monomer is dicyclopentadiene.

3. The method of claim 1 wherein the catalyst is of the formula

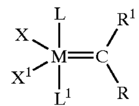

wherein:

M is ruthenium or osmium;

X and $X^1$ are either the same or different and are any anionic ligand;

L and $L^1$ are either the same or different and are neutral electron donor;

R and $R^1$ are either the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein each of the substituents is substituted or unsubstituted.

4. The method of claim 3 wherein the substituent group is substituted with one or more substituted or unsubstituted moieties selected from the group consisting of $C_1$–$C_{10}$ alkyl, $C_1$–$C_{10}$ alkoxy, and aryl.

5. The method of claim 3 wherein R is hydrogen and $R^1$ is selected from the group consisting of $C_1$–$C_{20}$ alkyl, $C_2$–$C_{20}$ alkenyl, aryl, unsubstituted phenyl, substituted phenyl, unsubstituted vinyl, and substituted vinyl; and wherein the substituted phenyl and substituted vinyl are each independently substituted with one or more groups selected from the group consisting of $C_1$–$C_5$ alkyl, $C_1$–$C_5$ alkoxy, phenyl, hydroxyl, thiol, ketone, aldehyde, ester, ether, amine, imine, amide, nitro, carboxylic acid, disulfide, carbonate, isocyanate, carbodiimide, carboalkoxy, and halogen.

6. The method of claim 3 wherein L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether.

7. The method of claim 3 wherein L and $L^1$ are each a phosphine of the formula $PR^3R^4R^5$ wherein $R^3$, $R^4$, and $R^5$ are each independently selected from the group consisting of aryl and $C_1$–$C_{10}$ alkyl.

8. The method of claim 3 wherein X and $X^1$ are each independently selected from the group consisting of hydrogen, halogen, substituted moiety and unsubstituted moiety, wherein the moiety is selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$-$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl.

9. The method of claim 3 wherein X and $X^1$ are each independently selected from the group consisting of halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate.

10. The method of claim 3 wherein X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

11. The method of claim 3 wherein $L^1$ has the general formula:

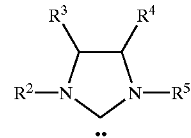

wherein:

$R^2$, $R^3$, $R^4$, and $R^5$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl.

12. The method of claim 11 wherein $R^3$ and $R^4$ together form a cycloalkyl or an aryl moiety.

13. The method of claim 11 wherein $R^3$ and $R^4$ are both hydrogen or phenyl and $R^2$ and $R^5$ are each independently substituted or unsubstituted aryl.

14. The method of claim 1 wherein the catalyst:monomer ratio is about 1:100 to about 1:1000000.

15. The method of claim 1 further comprising adding an inhibitor.

16. The method of claim 1 wherein the antioxidant is selected from the group consisting of 4,4'-methylenebis(2,6 di-tertiary-butylphenol), 1,3,5-trimethyl-2,4,6- tris(3,5-di-tert-butyl-4-hydroxybenzyl)benzene, and octadecyl-3-(3', 5',-di-tert-butyl-4'-hydroxyphenyl) propionate.

17. The method of claim 1 wherein the solvent is present in the amount of about 0.1% to about 15% by weight of the olefin monomer.

18. A method for dispersing a metathesis catalyst in an olefin to produce a catalyst-monomer mixture having a desired catalyst:monomer ratio comprising:

dispersing the catalyst within a dispersing carrier;

mixing the dispersed catalyst with an olefin monomer; and adding an antioxidant.

19. The method of claim 18 wherein the olefin monomer is dicyclopentadiene.

20. The method of claim 18 wherein the catalyst is of the formula

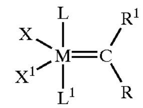

wherein:

M is ruthenium or osmium;

X and $X^1$ are either the same or different and are any anionic ligand;

L and $L^1$ are either the same or different and are neutral electron donor;

R and $R^1$ are either the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein each of the substituents is substituted or unsubstituted.

21. The method of claim 20 wherein R is hydrogen and $R^1$ is selected from the group consisting of $C_1$–$C_{20}$ alkyl, $C_2$–$C_{20}$ alkenyl, aryl, unsubstituted phenyl, substituted phenyl, unsubstituted vinyl, and substituted vinyl; and wherein the substituted phenyl and substituted vinyl are each independently substituted with one or more groups selected from the group consisting of $C_1$–$C_5$ alkyl, $C_1$–$C_5$ alkoxy, phenyl, hydroxyl, thiol, ketone, aldehyde, ester, ether, amine, imine, amide, nitro, carboxylic acid, disulfide, carbonate, isocyanate, carbodiimide, carboalkoxy, and halogen.

22. The method of claim 20 wherein L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether.

23. The method of claim 20 wherein L and $L^1$ are each a phosphine of the formula $PR^3R^4R^5$ wherein $R^3$, $R^4$, and $R^5$ are each independently selected from the group consisting of aryl and $C_1$–$C_{10}$ alkyl.

24. The method of claim 20 wherein X and $X^1$ are each independently selected from the group consisting of hydrogen, halogen, substituted moiety and unsubstituted moiety, wherein the moiety is selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl.

25. The method of claim 20 wherein $L^1$ has the general formula:

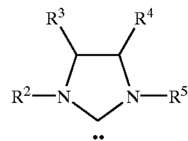

wherein:

$R^2$, $R^3$, $R^4$, and $R^5$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl.

26. The method of claim 25 wherein $R^3$ and $R^4$ together form a cycloalkyl or an aryl moiety.

27. The method of claim 25 wherein $R^3$ and $R^4$ are both hydrogen or phenyl and $R^2$ and $R^5$ are each independently substituted or unsubstituted aryl.

28. The method of claim 18 wherein the catalyst:monomer ratio is about 1:100 to about 1:1000000.

29. The method of claim 18 (further comprising adding an inhibitor.

30. The method of claim 18 wherein the antioxidant is selected from the group consisting of 4,4'-methylenebis(2,6 di-tertiary-butylphenol), 1,3,5-trimethyl-2,4,6-tris(3,5-di-tert-butyl-4-hydroxybenzyl)benzene, and octadecyl-3-(3',5',-di-tert-butyl-4'-hydroxyphenyl) propionate.

31. The method of claim 18 wherein the dispersing carrier is a hydrophobic solvent.

32. The method of claim 18 wherein the dispersing carrier is soybean oil or mineral oil.

33. The method of claim 18 wherein the dispersing carrier is a hydrophobic hydrocarbon.

34. The method of claim 18 wherein the dispersing carrier is present in the amount of about 0. 1% to about 15% by weight of the olefin monomer.

35. A method for dispersing a metathesis catalyst in an olefin to produce a catalyst-monomer mixture having a desired catalyst:monomer ratio comprising:

dispersing the catalyst within a solvent, wherein the solvent is soybean oil or mineral oil; and mixing the dispersed catalyst with an olefin monomer.

36. The method of claim 35 wherein the olefin monomer is dicyclopentadiene.

37. The method of claim 35 wherein the catalyst is of the formula

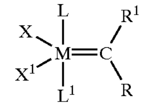

wherein:

M is ruthenium or osmium;

X and $X^1$ are either the same or different and are any anionic ligand;

L and $L^1$ are either the same or different and are neutral electron donor;

R and $R^1$ are either the same or different and are each independently hydrogen or a substituent selected from the group consisting of $C_1$–C20 alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein each of the substituents is substituted or unsubstituted.

38. The method of claim 37 wherein the substituent group is substituted with one or more substituted or unsubstituted moieties selected from the group consisting of $C_1$–$C_{10}$ alkyl, $C_1$–$C_{10}$ alkoxy, and aryl.

39. The method of claim 38 wherein R is hydrogen and $R^1$ is selected from the group consisting of $C_1$–$C_{20}$ alkyl, $C_2$–$C_{20}$ alkenyl, aryl, unsubstituted phenyl, substituted phenyl, unsubstituted vinyl, and substituted vinyl; and wherein the substituted phenyl and substituted vinyl are each independently substituted with one or more groups selected from the group consisting of $C_1$–$C_5$ alkyl, C,-$C_5$ alkoxy, phenyl, hydroxyl, thiol, ketone, aldehyde, ester, ether, amine, imine, amide, nitro, carboxylic acid, disulfide, carbonate, isocyanate, carbodiimide, carboalkoxy, and halogen.

40. The method of claim 37 wherein L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether.

41. The method of claim 37 wherein L and $L^1$ are each a phosphine of the formula $PR^3R^4R^5$ wherein $R^3$, $R^4$, and $R^5$-are each independently selected from the group consisting of aryl and $C_1$–$C_{10}$ alkyl.

42. The method of claim 37 wherein X and $X^1$ are each independently selected from the group consisting of hydrogen, halogen, substituted moiety and unsubstituted moiety, wherein the moiety is selected from the group consisting of Cl,-$C_{20}$ alkyl, aryl, $C_1$–$C_{20}$ alkoxide, aryloxide, $C_3$–$C_{20}$ alkyldiketonate, aryidiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl.

43. The method of claims 37 wherein X and $X^1$ are each independently selected from the group consisting of halide, benzoate, $C_1$–$C_5$ carboxylate, C,-$C_5$ alkyl, phenoxy, $C_1$–C5 alkoxy, $C_1$–$C_5$ alkylthio, aryl, and $C_1$–$C_5$ alkyl sulfonate.

44. The method of claim 37 wherein X and $X^1$ are each independently selected from the group consisting of halide, $CF_3CO_2$, $CH_3CO_2$, $CFH_2CO_2$, $(CH_3)\ _3CO$, $(CF_3)_2(CH_3)$ CO, $(CF_3)(CH_3)\ _2CO$, PhO, MeO, EtO, tosylate, mesylate, and trifluoromethanesulfonate.

45. The method of claim 37 wherein $L^1$ has the general formula:

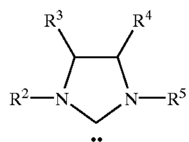

wherein:

$R^2$, $R^3$, $R^4$, and $R^5$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl.

46. The method of claim 45 wherein $R^3$ and $R^4$ together form a cycloalkyl or an aryl moiety.

47. The method of claim 45 wherein $R^3$ and $R^4$ are both hydrogen or phenyl and $R^2$ and R5 are each independently substituted or unsubstituted aryl.

48. The method of claim 35 wherein the catalyst:monomer ratio is about 1:100 to about 1:1000000.

49. The method of claim 35 further comprising adding an inhibitor.

50. The method of claim 35 wherein the solvent is present in the amount of about 0.1% to about 15% by weight of the olefin monomer.

* * * * *